United States Patent
Patel et al.

(10) Patent No.: US 10,058,461 B1
(45) Date of Patent: Aug. 28, 2018

(54) LOWER SURFACE FRICTION ABSORBENT ARTICLES AND RELATED METHODS THEREFOR

(71) Applicant: KPR U.S., LLC, Mansfield, MA (US)

(72) Inventors: Harish A. Patel, Norfolk, MA (US); Vishal Narvekar, Mansfield, MA (US); Kevin Corley, Reading, MA (US)

(73) Assignee: KPR U.S LLC, Mansfield, MA (US)

( * ) Notice: Subject to any disclaimer, the term of this patent is extended or adjusted under 35 U.S.C. 154(b) by 637 days.

(21) Appl. No.: 14/040,785

(22) Filed: Sep. 30, 2013

Related U.S. Application Data (60) Provisional application No. 61/772,437, filed on Mar. 4, 2013.

(51) Int. Cl.
  *A61F 13/15* (2006.01)
  *A61F 13/20* (2006.01)
  *A61F 13/53* (2006.01)

(52) U.S. Cl.
  CPC ........ *A61F 13/53* (2013.01); *A61F 13/15577* (2013.01)

(58) Field of Classification Search
  CPC ............ A61F 13/15; A61F 2013/53043; A61F 2013/530481; A61F 2013/53051; A61F 2013/530562
  See application file for complete search history.

(56) References Cited

U.S. PATENT DOCUMENTS

| | | | |
|---|---|---|---|
| 4,094,319 A * | 6/1978 | Joa ........................ | A61F 13/515 604/372 |
| 5,533,991 A | 7/1996 | Kirby et al. | |
| 5,716,351 A | 2/1998 | Roe et al. | |
| 5,782,819 A | 7/1998 | Tanzer et al. | |
| 5,913,850 A * | 6/1999 | D'Alessio ......... | A61F 13/15203 604/370 |
| 6,290,686 B1 * | 9/2001 | Tanzer ................ | A61F 13/5323 604/358 |
| 6,455,753 B1 * | 9/2002 | Glaug ............... | A61F 13/53717 604/368 |
| 6,573,422 B1 * | 6/2003 | Rosenfeld ......... | A61F 13/15658 604/368 |
| 6,641,568 B2 | 11/2003 | Ashton et al. | |
| 6,911,407 B2 | 6/2005 | Sherrod et al. | |
| 6,918,900 B2 | 7/2005 | Johnson | |
| 6,932,802 B2 | 8/2005 | Luizzi, Jr. et al. | |
| 7,074,215 B2 * | 7/2006 | Ashton ................. | A61F 13/496 604/389 |
| 7,345,215 B2 * | 3/2008 | Fernfors ............... | A61F 13/539 128/891 |
| 7,794,440 B2 * | 9/2010 | Schuehle .............. | A61F 13/495 604/383 |
| 7,833,208 B2 | 11/2010 | Koenig et al. | |
| 7,919,669 B2 | 4/2011 | Roe et al. | |

(Continued)

OTHER PUBLICATIONS

"Bicomponent." Merriam-Webster.com. Merriam-Webster, n.d. Web. Oct. 18, 2017.*

*Primary Examiner* — Michele M Kidwell
(74) *Attorney, Agent, or Firm* — Nicole M. Creegan (57) ABSTRACT

An absorbent article includes a fluid pervious top sheet, a fluid impervious bottom sheet, and an absorbent core positioned therebetween. The top sheet comprises a plurality of bicomponent fibers having target friction characteristics.

19 Claims, 4 Drawing Sheets

(56) References Cited

U.S. PATENT DOCUMENTS

| | | | |
|---|---|---|---|
| 7,947,367 B2* | 5/2011 | Poon | C08F 210/16 |
| | | | 428/394 |
| 8,318,073 B2 | 11/2012 | Schneider | |
| 8,353,888 B2 | 1/2013 | Koenig et al. | |
| 2003/0220048 A1* | 11/2003 | Toro | A61F 13/51462 |
| | | | 450/57 |
| 2003/0232556 A1 | 12/2003 | Toro et al. | |
| 2005/0165375 A1* | 7/2005 | Fernfors | A61F 13/539 |
| | | | 604/378 |
| 2005/0273070 A1 | 12/2005 | Olson et al. | |
| 2006/0081348 A1* | 4/2006 | Graef | A61F 13/15617 |
| | | | 162/141 |
| 2006/0142722 A1* | 6/2006 | Koenig | A61F 13/82 |
| | | | 604/385.03 |
| 2006/0247599 A1* | 11/2006 | Mullen | A61F 13/505 |
| | | | 604/393 |
| 2007/0142813 A1 | 6/2007 | Sperl | |
| 2011/0022016 A1 | 1/2011 | Koenig et al. | |
| 2011/0152813 A1* | 6/2011 | Ellingson | A61F 13/532 |
| | | | 604/374 |
| 2011/0160526 A1* | 6/2011 | Zunker | A61F 2/005 |
| | | | 600/29 |
| 2011/0282313 A1* | 11/2011 | Lu | A61F 13/5148 |
| | | | 604/378 |
| 2014/0065373 A1* | 3/2014 | Narvekar | B32B 3/30 |
| | | | 428/166 |
| 2014/0072788 A1* | 3/2014 | Burkhart | D04H 3/163 |
| | | | 428/219 |

\* cited by examiner

Artificial skin attachment device

Underpad Topsheet surface

FIG. 6

Artificial skin substrate

Screw to tighten stainless steel wire

Stainless steel wire

Screw to tighten Artificial skin substrate

LOWER SURFACE FRICTION ABSORBENT ARTICLES AND RELATED METHODS THEREFOR

CROSS-REFERENCE TO RELATED APPLICATION

This application claims the benefit of priority under 35 U.S.C. § 119 to U.S. Patent Application No. 61/772,437, titled ABSORBENT ARTICLES AND RELATED METHODS THEREFOR, which was filed on Mar. 4, 2013, the entirety of which is incorporated herein by reference for all purposes.

BACKGROUND

Technical Field

The present disclosure relates generally to absorbent products or articles including underpads having an absorbent core and a top sheet having a low coefficient of friction.

Related Art

Absorbent articles are used to collect and/or absorb body fluid discharge, such as, blood, menses, urine, aqueous body fluids, mucus, and cellular debris. Absorbent articles include, for example, disposable diapers, adult incontinent pads, sanitary napkins, party-liners, and the like, that are generally worn in cooperation with garments and disposed against a body surface, by infants and/or adults. Underpads as absorbent articles are suitable for use with patient bedding, for example, as a disposable absorbent article placed under a patient.

SUMMARY

The articles and methods disclosed herein provide improved usability by having an absorbent core with a top sheet or top layer having a low coefficient of friction. Some aspects of the invention can pertain to absorbent articles having a top sheet or top layer with a tailored coefficient of friction. Some further aspects of the invention can pertain to absorbent articles having a top sheet that exhibits friction characteristics that at least partially inhibits unintended initiation of sliding of a subject in contact with the top sheet while providing a lower resistance when the subject is actively sliding on the top sheet. Thus, some embodiments of the disclosed absorbent articles can have a top sheet with at least a predetermined static coefficient of friction and less than a predetermined kinetic coefficient of friction. In some cases, the static coefficient of friction in a range of from about 0.8 to about 1; and in some further cases, the kinetic coefficient of friction is in a range of from about 0.5 to about 0.7.

One or more aspects of the invention can pertain to an absorbent article comprising a fluid pervious top sheet, a fluid impervious bottom sheet or back sheet, and an absorbent core. One or more aspects of the disclosure can pertain to a method of fabricating an absorbent article. The method can comprise providing a fluid pervious top sheet; providing a fluid impervious bottom sheet; and positioning an absorbent core between the top sheet and the bottom sheet. The top sheet, in one or more embodiments pertinent to one or more aspects of the invention, can comprise bicomponent fibers. In some cases, the absorbent core can have at least one superabsorbent section comprising, consisting of, or consisting essentially of superabsorbent polymer particles. In some configurations pertinent to one or more aspects of the invention, at least one of the superabsorbent sections can define a first zone comprising a first amount of superabsorbent polymer particles and at least another of the plurality of superabsorbent sections defines a second zone comprising a second amount of superabsorbent polymer particles, the first amount of superabsorbent polymer particles is typically greater than the second amount of superabsorbent polymer particles. In some configurations pertinent to one or more aspects of the invention, the first zone can comprise about at least about 70 wt % of superabsorbent polymer particles and less than about 30 wt % fluff pulp. In some configurations pertinent to one or more aspects of the invention, the absorbent article can further comprise an absorbent layer disposed between the bottom sheet and the absorbent core. In some configurations pertinent to one or more aspects of the invention, the absorbent layer can comprise a matrix of fluff pulp.

DESCRIPTION OF THE DRAWINGS

Various features of the presently disclosed absorbent article will be described with reference to an exemplary underpad represented in the accompanying drawings wherein like reference numerals identify similar or identical elements in each of the several views to show the various features and advantages thereof; in the drawings.

DETAILED DESCRIPTION

The following discussion includes a description of the presently disclosed absorbent articles in accordance with the principles of the present disclosure. The absorbent article can include a substrate upon and within which fluid discharge, e.g., liquid insult, may be applied and absorbed. For illustrative purposes, the absorbent article will be discussed in terms of a patient care underpad; however, the presently disclosed absorbent articles may be any absorbent product such as, for example, juvenile diapers and training pants, feminine menstrual pads, adult incontinence products, pet training pads, and other disposable products utilized to absorb fluids. Absorbent articles with certain advantageous features typically include a multi-layer arrangement with a fluid permeable top sheet or top layer for engaging the body surface, a fluid impermeable back sheet for preventing fluid leakage through the article, and an absorbent core disposed therebetween. The absorbent core can be comprised of a liquid retention material that faces the body surface. The absorbent core can include loosely formed cellulosic fibers, superabsorbent fibers, superabsorbent particles, or combinations thereof in a continuous or embossed pattern for acquiring and storing fluid discharge. Fluid discharge leakage may result from over-saturation of the absorbent core and/or from pooled fluid run off. For example, during a fluid discharge, it is common for urine deposited onto the top sheet to pool before it penetrates the absorbent core. If pooling occurs, urine will not be absorbed and fluid run off may occur, resulting in undesirable leakage from the absorbent article.

In the present disclosure, the term "proximal" or "body side" will refer to the portion of the absorbent article that is closer to a user while the term "distal" or "fixture side" will refer to the portion of the absorbent article that is away from the user. The term "body side" should not be interpreted to necessarily refer to contact with the body of the user, but rather refers to the side that faces toward the body of the user, regardless of whether the absorbent article is actually being used and regardless of whether there are or may be intervening layers between the absorbent article and the body of the user. Likewise, the term "fixture side" should not be interpreted to mean affixed to an article, e.g., garment, bedding, bed, chair, wheelchair, but rather refers to the side that faces away from the body of the user, and therefore towards any fixture which the user is utilizing, regardless of whether there are or may be intervening layers between the absorbent article and the fixture and regardless of whether any fixture may be present or may be utilized. Further, the term "average" refers to the result obtained by dividing the sum of at least five measurements by the number of measurements.

Figure 1:
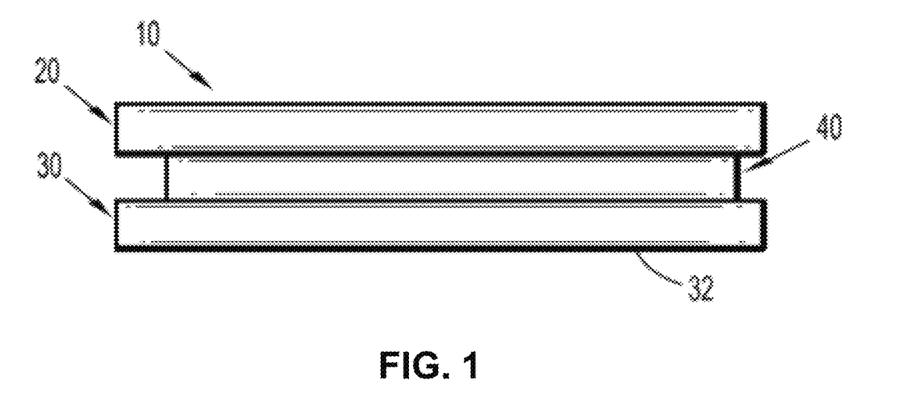
FIG. 1 is a schematic illustration showing an elevational view of a cross-section of an underpad in accordance with one or more aspects of the disclosed absorbent article.

FIG. 1 exemplarily illustrates a cross-section of a portion of an underpad 10, as an example of an absorbent article in accordance with the present disclosure, including a top sheet 20, which is typically proximal to a patient, a bottom or back sheet 30, which is typically at a distal side of the article, and an absorbent core 40 disposed between the top sheet 20 and the back sheet 30. The size and shape of the top sheet, the back sheet, and the absorbent core typically depends on several considerations including the design and intended usage selected of the absorbent article. Edge portions of the back sheet 30 may be folded over a portion of the top sheet 20 to form a fluid-tight fold-over edge seal.

Back sheet 30 can be a fluid impervious layer for preventing liquid absorbed and contained in the absorbent core 40 from wetting articles which contact the underpad, such as but not limited to, undergarments, pants, pajamas, and bed sheets. Back sheet 30 may be a woven material; a nonwoven material; a liquid-impervious fabric; a cellulosic film; a polymeric film such as a thermoplastic film of polyethylene or polypropylene; an impregnated fluid repellent paper; a composite material, e.g., a polylaminate, such as a film-coated non-woven material; or combinations thereof. Back sheet 30, or at least portions thereof, may be embossed or may have matte-finish with a cloth-like appearance. Any of the variants of the back sheet may be or colored and may have markings or indicia that can facilitate identification of the article. Further non-limiting configurations of the back sheet 30 may involve breathable variants that allow at least some vapor to escape or pass from the absorbent core 40 while preventing fluid discharge, e.g., liquid, from passing therethrough. In some cases, the back sheet can be a composite laminate comprising or consisting essentially of a vapor-impermeable polymeric film with a non-woven material adhered thereto by an adhesive. Such a composite laminate can provide the back sheet with one or more desirable physical properties and performance characteristics by selective combinations the film and the non-woven layer assembly. For example, the back sheet can be rendered vapor permeable by introducing pores through the vapor-impermeable film. Thus, the back sheet can be constructed to have variable regions of vapor permeability. For example, the back sheet can have pores or perforations at areas which do not overlap or do not superimpose on the areas of the absorbent core. Further, the size and density of the pores can be varied to selectively provide the one or more physical and performance characteristics. Further, multi-film laminate assemblies may be utilized as at least a portion of the back sheet. For example, the back sheet can have a first film layer along with a second film layer. The first film can be first vapor-permeable, liquid-impermeable film and the second film can be a second vapor-permeable film with a moisture vapor transmission rate (MVTR) that differs from an MVTR of the first film.

A layer of adhesive material can secure the top sheet to the absorbent core and, in some cases, to peripheral regions of the back sheet. Likewise, a layer of adhesive material can secure the absorbent core to the back sheet. Suitable adhesive materials include, for example, acrylic-based materials. In other cases, at least a portion the top sheet 20 can be thermally bonded to contacting areas of peripheral regions of the back sheet. In other cases, a thermal bonding layer can be utilized to secure peripheral regions of the top sheet to corresponding contacting peripheral areas of the back sheet. Thus, the absorbent layer or core can be surrounded by peripheral areas that bond or secure together peripheral areas of the top sheet and peripheral areas of the back sheet. Thermal bonding can be effected by, for example, melting a portion of the polymeric material of any of the top sheet and the back sheet, or both, and allowing the melted polymeric material to solidify. Thermal bonding can also be effected with binding agents, such as binding powders or binding fibers, and utilizing hot calendering, belt calendering, hot air or radiant melting, or ultrasonic techniques.

Back sheet 30 may be attachable or configured to be attached removably to an article or fixture (not explicitly shown) such as an undergarment or other piece of clothing, a chair, a bed or bedding, a wheelchair or any other suitable fixture in which a patient may require the use of a disposable absorbent article. For example, the back sheet 30 can include one or more attachment devices (not shown) such as, for example, one or more adhesive patches or strips, one or more hook-and-loop type connectors, one or more attachment straps, one or more clip connectors, combinations thereof, or other suitable connector that retains the underpad 10 to the fixture. For example, the attachment devices may be affixed to a fixture side 32 of the back sheet 30, and may extend along a portion, or the entire length and/or width of the underpad 10. Affixing the one or more attachment devices can be effected by, for example, adhesively securing the various attachment devices to the absorbent article.

The absorbent core 40 typically includes a fluid absorbing material or composition made from absorbent materials such as but not limited to foams; nonwoven composite fabrics; hydrogels; cellulosic fabrics; superabsorbent polymers; woven fabrics; tissue, paper; inherently hydrophilic foams, e.g., viscose rayon foam; natural or synthetic foamed polymeric material, e.g., polyurethane, polyether, or styrene/ butadiene rubber foams which have been rendered hydrophilic or readily wettable; comminuted wood pulp; cotton linters and cotton wool of any grade; rayon fibers; cotton staple; bleached or unbleached-creped tissue; and combinations and composites thereof.

The thickness of the absorbent core 40 may vary to provide a desirable or target performance or absorbance characteristic. Thus, one or more aspects of the absorbent core can involve thicker and thinner areas. For example, the absorbent core 40 may have a thicker portion at a central or inner portion which can be bounded or surrounded by a thinner absorbent portion. Alternatives and variants of the absorbent core can involve concentric regions of alternating thicker and thinner portions thereof. Each of the various thicker and thinner concentric portions, which may embodied as circular rings or other geometrical-defined constructs, may have predetermined or tailored increasing or decreasing capacities and, in some cases, may have predetermined or tailored increasing or decreasing liquid absorption rates. Thus, the various absorbent articles disclosed herein may be configured to have tailored absorbing characteristics.

The absorbent core 40 can include a fibrous matrix of wood fiber or fluff material. In some embodiments, the absorbent core 40 includes a fibrous matrix of fluff pulp into or onto which superabsorbent polymer (SAP) particles or fiber are dispersed. The SAP material may be continuously or discontinuously distributed through the absorbent core 40. For example, the SAP material may be uniformly distributed throughout the absorbent core or may be distributed a manner which creates a distribution gradient of an amount of SAP material, relative to, for example, one or more dimensions or directions of the core or the the absorbent article. In a particular embodiment, the absorbent core can have a greater amount of SAP at a central or inner portion relative to a peripheral or outer portion of the absorbent core. As noted above, the various absorbent articles disclosed herein may thus be configured to have tailored absorbent characteristic by varying the relative amounts of SAP as well as relative amounts of any additional absorbing materials, such as fluff pulp.

Figure 2:
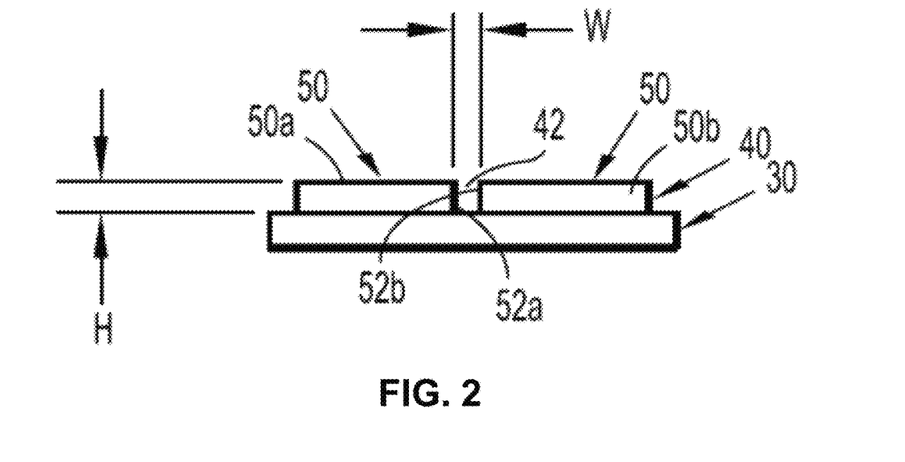
FIG. 2 is a schematic illustration showing an elevational view of a portion of an underpad in accordance with one or more aspects of the disclosed absorbent article.

In FIG. 2, the absorbent core 40 is exemplarily illustrated as being disposed at about the center of the underpad 10 (shown in relation to the back sheet 30 and without the top sheet 20) and is composed of a plurality of spaced superabsorbent sections 50 defining a channel 42 therebetween. Channel 42 allows fluid discharge to be absorbed by the aligned superabsorbent sections 50 of the absorbent core 40 while also preventing fluid discharge from flowing outside of the underpad 10. Superabsorbent sections 50 can comprise, consist of, or consist essentially of one or more types of SAP material. Channel 42 can extend along a longitudinal axis, e.g., along a machine direction, along the entire length of the absorbent core 40. In the exemplarily illustrated embodiment, a first superabsorbent section 50a and a second superabsorbent section 50b are positioned on opposing sides of channel 42 such that longitudinally extending sides 52a and 52b define a dimension, e.g., a width W, of channel 42. The width W, of channel 42 may be in a range of from about 0.1 mm to about 10 mm; and in further embodiments, width W may be in a range of from about 0.25 mm to about 8 mm; and in some embodiments, width W may be in a range of from about 1 mm to about 5 mm. Channel 42 typically also has a second dimension, e.g., a height H, that extends through the absorbent core 40. The height H of the channel 42 may extend entirely or through only a portion of the absorbent core 40. The width W and the height H of any of the channels 42 of the core may vary depending upon the application or use of the absorbent article. This further aspect may thus be utilized to tailor the absorbent characteristics of the absorbent article, with or without the other configurable features disclosed herein.

The first and second superabsorbent sections 50a and 50b can include an inner zone (not shown) positioned proximate to the channel 42 including a higher distribution of SAP particles than an outer zone thereof (not shown). The inner zone of the first and second superabsorbent sections 50a and 50b, respectively, can include at least half, if not a major portion of the SAP particles, relative to the total amount of SAP in the absorbent article. For example, the inner zone can include about 50% to about 90% (by weight) of the SAP particles, and in some embodiments, about 70% (by weight) of the SAP particles can be distributed in the inner zone of the superabsorbent sections 50. While the inner and outer zones of the first and second superabsorbent sections can linearly extend along the length of the absorbent core 40, the inner zone may be provided in a center portion of the superabsorbent sections while the outer zone can be provided around a periphery thereof in a radiating distribution pattern.

In use, the underpad 10 is placed directly under a user such that the center of the underpad 10 is positioned to receive fluid discharge from the user. When the underpad 10 receives fluid discharge, such as an insult of fluid, from the user, a majority of the fluid passes through the top sheet 20 and is preferably absorbed by the absorbent core 40. The alignment of the superabsorbent sections 50 and the channel 42, as well as the distribution pattern of the SAP particles within the superabsorbent sections 50, can facilitate migration and/or wicking of the fluid discharge into the absorbent core 40, or the various portions or zones thereof. In addition, the channel 42 may allow for easy folding of the underpad 10 about the center thereof.

The underpad is typically discarded after one insult.

One or more further advantageous aspects pertain to absorbent articles having patient facing or patient contacting surfaces that exhibit low friction characteristics. In accordance with such further aspects, some embodiment of the absorbent article can have a top sheet 20 that is a fluid pervious layer for permitting liquid, e.g., menses or urine, to penetrate readily through its thickness and preferably is compliant and soft to the touch so that it does not irritate skin or at least reduces the likelihood causing skin irritation. Top sheet 20 may be manufactured from a wide range of materials such as woven and non-woven materials, e.g., a non-woven web of fibers; polymeric materials such as thermoplastic films having apertures, plastic films having apertures, and hydro-formed thermoplastic films; porous foams; reticulated foams; reticulated thermoplastic films; and thermoplastic scrims. Suitable fibers that may be utilized to construct woven and non-woven materials include, for example, natural fibers, e.g., wood or cotton fibers, synthetic fibers, e.g., polymeric fibers such as polyester, polypropylene, or polyethylene fibers, and combinations of natural and synthetic fibers. In embodiments in which the top sheet 20 is a non-woven web, the web may be spun-bonded, carded, wet-laid, melt-blown, hydro-entangled, or formed using any method suitable for forming a non-woven web.

In accordance with further embodiments of the disclosure, at least a portion of the liquid pervious top sheet can be comprised of a nonwoven fibrous layer of polyolefinic fibers. The fibers can be multicomponent fibers. At least a portion of the fibers of at least a portion of the top sheet 20 can comprise bicomponent fibers having a first component that has a first thermomechanical property and a second component that has a second thermomechanical property that differs from the first thermomechanical property. The thermomechanical property can be any one of first fusion point, melting temperature or range of melting temperature, crystallization temperature, and glass transition temperature. The first thermomechanical property can be less than the second thermomechanical property. For example, the first component can have a first fusion point and a second component can have a second fusion point, wherein the first fusion point is less than the second fusion point. Conversely, the first component can have a first melting temperature range and a second component with a second melting temperature range, wherein at least a portion of the first melting temperature range is less than the second melting temperature range.

Specific configurations of the top sheet can thus involve embodiments wherein the bicomponent fibers with a sheath that is comprised of a first component surrounding a core that is comprised of a second component with the first component having a lower melting temperature than the melting temperature of the second component. Further specific configurations can involve having at least a portion of the top sheet comprising thermobondable polymeric bicomponent fibers with a high-melting point core and a low-melting point sheath that substantially surrounds the core.

The top sheet can have any desired basis weight based on, for example, a particular use of the absorbent article. For example, the basis weight of the top sheet can be in a range of from about 10 gsm to about 30 gsm.

In some configurations, the top sheet comprises a first monolithic fiber comprised of a first polyolefin and a second monolithic fiber comprised of a second polyolefin. In other configurations, the top sheet consists essentially of a first fiber comprised of a first polyolefin and a second fiber comprised of a second polyolefin. In further configurations, the top sheet consists of a first fiber of a first polyolefin and a second fiber of a second polyolefin. Typically, at least one thermomechanical property of the first polyolefin differs from at least one thermomechanical property of the second polyolefin. For example, the first polyolefin can have a melting temperature that is less than a melting temperature of the second polyolefin. In other cases, the first polyolefin can have a melting temperature that is greater than a melting temperature of the second polyolefin. In yet other cases, the first polyolefin has a first range of melting temperature and the second polyolefin has a second range of melting temperature, at least a portion of the second melting temperature range is greater than the first inciting temperature range. The amount of the first fibers in the top sheet can be in a range of from about 10 wt % to about 99 wt % but can be in a range of from about 40 wt % to about 80 wt %, and in specific variants, is in a range of from about 45% wt % to about 55 wt %, wherein the balance is the second fiber.

In still further configurations, at least a portion of the top sheet can be comprised of bicomponent fibers. For example, the top sheet can comprise monolithic fibers comprised of a first polyolefin and can further comprise bicomponent fibers with a sheath comprised of the first polyolefin that substantially surrounds a core that can be comprised of a second polyolefin. In some specific variants, the first polyolefin has melting temperature that is less than a melting temperature of the second polyolefin. Alternatively, the first polyolefin can have a melting temperature that is greater than a melting temperature of the second polyolefin. In yet further variants, the first polyolefin has a first range of melting temperature and the second polyolefin has a second range of melting temperature wherein at least a portion of the second melting temperature range is greater than the first melting temperature range. In any of such variant configurations, the amount of the bicomponent fibers in the top sheet can be in a range of from about 10 wt % to about 99 wt % but can be in a range of from about 40 wt % to about 60 wt %, and in specific variants, is in a range of from about 45% wt % to about 55 wt %. In some particular configurations, the amount of bicomponent fibers is at least about 50 wt %. However, in some particular embodiments the top sheet 20 consists essentially of bicomponent fibers but in some particular embodiments, top sheet 20 consists of bicomponent fibers. Thus, in some cases, the top sheet can be 100 wt % bicomponent fibers. Particular configurations, however, can involve the top sheet consisting of or consisting essentially of bicomponent fibers having bicomponent fibers in an amount that tailored to provide a target coefficient of friction. For example, the absorbent article can comprise a top sheet, which can comprise, consist essentially of or consist of bicomponent fibers, which is adhered to the absorbent core, wherein the amount of bicomponent fibers is sufficient to provide an average kinetic coefficient of friction of less than about 0.7 and an average static coefficient of friction of at least about 0.8. Further, in some embodiments, the absorbent article can comprise a top sheet, which can comprise, consist essentially of, or consist of bicomponent fibers, which is adhered to the absorbent core, wherein the amount of bicomponent fibers is sufficient to provide the top sheet with an average kinetic coefficient of friction in a range of from about 0.7 to about 0.5 and an average static coefficient of friction in a range of from about 0.8 to about 1, when in contact with a polyethylene-based surface. In some embodiments, tailoring to achieve the target static or kinetic coefficient of friction can be effected by altering the amount of bicomponent fibers relative to the amount of non-bicomponent fibers.

The bicomponent fibers typically have a core of a first polyolefin and a sheath around the core of a second polyolefin. Top sheet 20 can thus consist essentially of bicomponent fibers having a core of a first polyolefin and a sheath around the core of a second polyolefin. Other variants of the top sheet can involve utilizing bicomponent fibers having a sheath of a polyolefin that substantially surrounds core of the same polyolefin except that at least one thermomechanical property of the sheath polyolefin differs from a thermomechanical property of the core polyolefin. For example, the sheath polyolefin may have a crystallization temperature or an average molecular weight that is greater than a crystallization temperature or an average molecular weight of the core polyolefin. Particular configurations can thus involve the top sheet consisting of or consisting essentially of bicomponent fibers having a crystallization temperature or a range of crystallization temperature that is tailored to provide a target coefficient of friction. For example, the absorbent article can comprise a top sheet, which can comprise, consist essentially of, or consist of bicomponent fibers, which is adhered to the absorbent core, wherein the bicomponent fibers is made of a polyolefin with a degree of crystallinity sufficient provide an average kinetic coefficient of friction of less than about 0.7 and an average static coefficient of friction of at least about 0.8. In further embodiments, the absorbent article can comprise a top sheet, which can comprise, consist essentially of, or consist of bicomponent fibers, wherein the amount of bicomponent fibers in the top sheet is sufficient to provide the top sheet with an average kinetic coefficient of friction in a range of from about 0.7 to about 0.5 and an average static coefficient of friction in a range of from about 0.8 to about 1, against a polyethylene-based surface.

Figure 3:
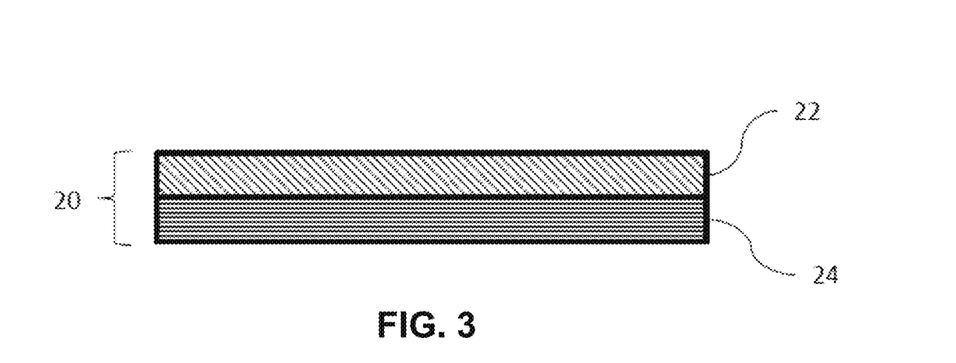
FIG. 3 is a schematic illustration showing a portion of a top sheet that may be utilized in accordance with one or more aspects of the disclosed absorbent article.
Figure 4:
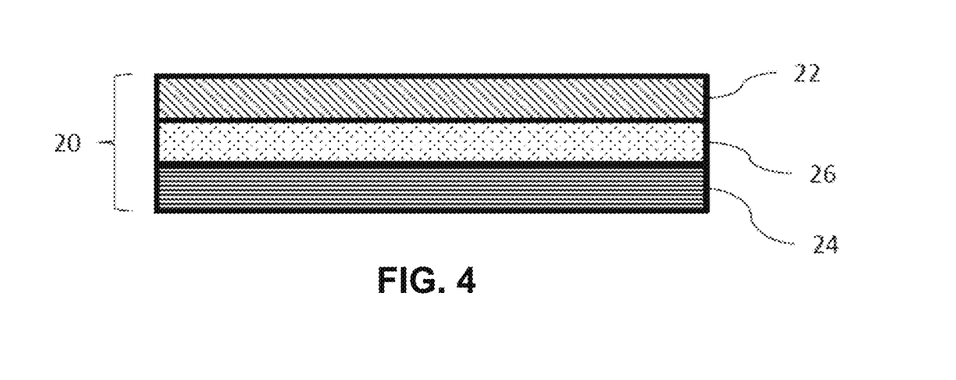
FIG. 4 is a schematic illustration showing a portion of a top sheet as a variant that may be utilized in accordance with one or more aspects of the disclosed absorbent article.

In some configurations, the top sheet 20 can comprise a plurality of layers. For example, as illustrated in FIGS. 3 and 4, the top sheet 20 can comprise a first layer 22, preferably as the body side layer, consisting of or consisting essentially of bicomponent fibers, and a second layer 24, typically a distal second layer, comprising or consisting of monocomponent fibers. In some particular configurations of the top sheet, the second layer 24 can consist of spun bond monocomponent fibers of polyolefin, which is preferably a polyethylene, and can be the same polyethylene of the sheath of the bicomponent fibers of the first layer 22. The various layers of the top sheet 20 can be at least partially thermally bonded to each other. For example, substantially all of a contacting area of the first layer 22 can be thermally bonded to substantially all of a corresponding contacting area of the second layer 24. In other cases, however, only portions of contacting regions between the first and the second layers are thermally bonded. In other particular configurations of the top sheet 20, the second layer 24 can comprise, consist of, or consist essentially of melt-blown monocomponent fibers of polyolefin, which can be the same polyethylene of the sheath of the bicomponent fibers of the first layer 22. In still other configurations, the top sheet 20 can comprise a first layer 22, preferably the body side layer comprising, consisting of, or consisting essentially of bicomponent fibers, a second layer 24 comprising, consisting of, or consisting essentially of monocomponent fibers, and a distal, third layer 26 of monocomponent fibers which can be the same or have a different composition as the fibers of the second layer 24. For example, the third layer 26 can comprise, consist of, or consist essentially of melt-blown monocomponent polyolefin fibers while the second layer 24 can comprise, consist of, or consist essentially of spun-bon or melt-blown monocomponent polyolefin fibers. Likewise, substantially all of the contacting area of the first layer 22 can be bonded, e.g., adhesively or thermally bonded, to substantially all of a first corresponding contacting area of the third layer 26 and substantially all of a second contacting area of the third layer 26 can be bonded, e.g., adhesively or thermally bonded, to substantially all of a corresponding contacting area of the second layer 24. In other cases, only portions of contacting regions between the first and third layers and between the third and second layers can be bonded. In some particular configurations, the top sheet can have a first or outer layer comprising, consisting essentially of, or consisting of spun bond bicomponent fibers, a second, intermediate, or middle layer comprising, consisting essentially of, or consisting of melt blown bicomponent fibers, and a third or inner layer comprising, consisting essentially of, or consisting of bicomponents fibers. In other particular configurations, the top sheet can have a first or outer layer comprising, consisting essentially of, or consisting of spun bond bicomponent fibers, a second, intermediate, or middle layer comprising, consisting essentially of, or consisting of spun bond bicomponent fibers, and a third or inner layer comprising, consisting essentially of, or consisting of bicomponents fibers. It is believed that the use of spun bond construction as the outer, contacting layer can provide desirable friction characteristic because spun bonded surfaces can have less roughness created by lesser amount of irregularities, or protrusions relative to the surface of melt blown layers. The bicomponent fibers of each of the layers can be substantially compositionally the same, e.g., the same polyolefin core and the same polyolefin sheath and within an acceptable manufacturing tolerance. The use of a plurality of layers can thus facilitate tailoring of the basis weight of the top sheet by, for example, utilizing a first layer with a first selected basis weight and additional one or more layers to supplement the first selected basis weight to provide the top sheet with the target basis weight.

The various fibers of the top sheet can be at least partially thermally bonded to other fibers thereof. Likewise the various fibers of the various layers top sheet can be at least partially thermally bonded to other fibers of the various other layers.

In any of the embodiments disclosed herein, the first polyolefin can be a polypropylene and the second polyolefin can be a polyethylene. In other embodiments, the first polyolefin can be a high-density polyethylene and the second polyolefin can be low-density polyethylene. For example, the sheath can comprise a linear low-density polyethylene having a density of less than or about 0.95 g/cm$^3$ and the core can comprise a high-density polyethylene having a density of greater than 0.95 g/cm$^3$.

EXAMPLE

The following example illustrates one or more aspects of the presently disclosed absorbent article and related methods therefor.

In this example, friction tests were performed on an underpad as the exemplary absorbent article. The underpad consisted of a top sheet with a basis weight of about 18 gsm, an airlaid absorbent core with a basis weight of about 130 gsm; and a moisture vapor permeable back sheet with a basis weight of about 56 gsm. The top sheet consisted of spun bond 100 wt % bicomponent fiber with a polypropylene (core) to polyethylene (sheath) ratio of 70:30 wt % from Providencia, Brazil. The absorbent core, from EAM Corporation, Jesup, Ga., had a SAP content of about 25 wt % and a centrifuge capacity in a range of from about 11-13. The back sheet consisted of about 24 gsm permeable film layer, about 30 gsm of a spun bond nonwoven which were secured together with about 2 gsm of a hotmelt adhesive. Rectangular test specimens of the underpad, about 4 inch (machine direction) by 10 inch (cross direction), were prepared.

Figure 5:
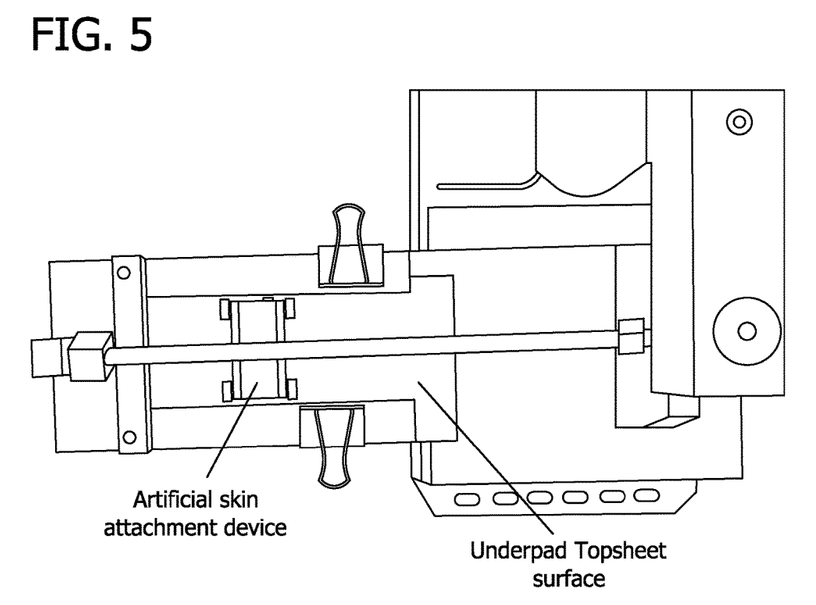
FIG. 5 is an illustration of a portion of a friction measurement apparatus utilized to measure friction properties of an underpad relative as pertinent to one or more aspects of the disclosed absorbent article.

FIG. 5 is a copy of a photograph of a portion of a friction measurement apparatus utilized in this example. For each friction measurement, an underpad specimen was secured in the friction measurement apparatus as shown. Each of the specimens was secured to the table of the friction measurement apparatus by clamping the sides of the specimen thereto to prevent the specimen from translating during the measurement procedure.

Figure 6:
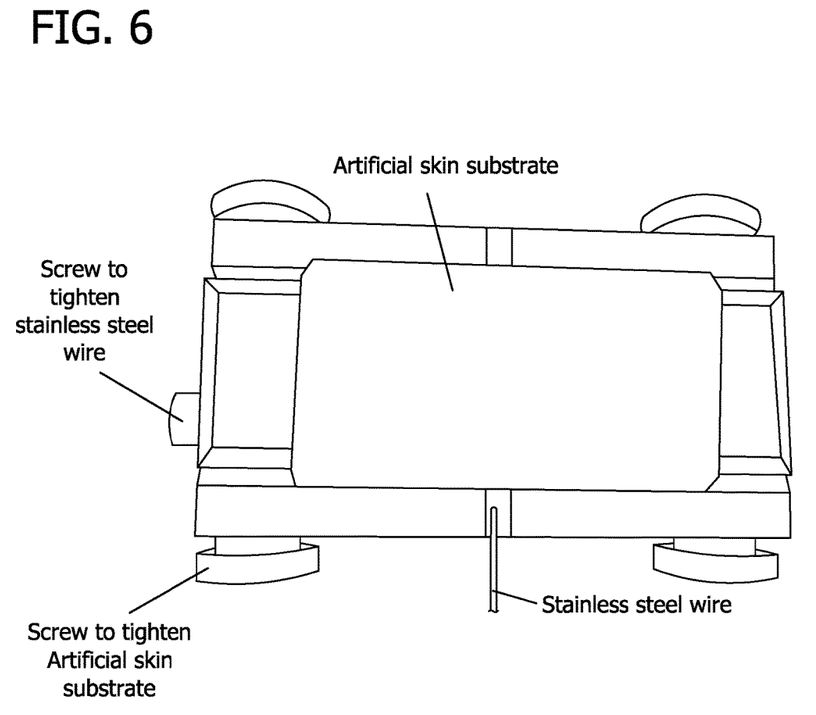
FIG. 6 is an illustration of an artificial skin attachment device of the friction measurement apparatus.

A polyethylene film substrate was utilized as a proxy for artificial skin in all the test runs. The polyethylene film was secured to an artificial skin attachment device by screw clamps as shown in FIG. 6. The artificial skin used in the test runs was a 5 mil LDPE film with a width of about 10 inches (CHARTER CI-100) from DermaMed Coatings Co. LLC, Tallmadge, Ohio.

The exposed surface of the secured artificial skin was placed on the exposed surface of the top sheet of the secured underpad. A steel wire was connected to the artificial skin attachment device and opposite end thereof was connected to a load cell, which was controlled by a TA.XT.PLUS texture analyzer, from Texture Technologies Corporation, Scarsdale, N.Y. The analyzer was calibrated with a 3 Kg mass.

Figure 7:
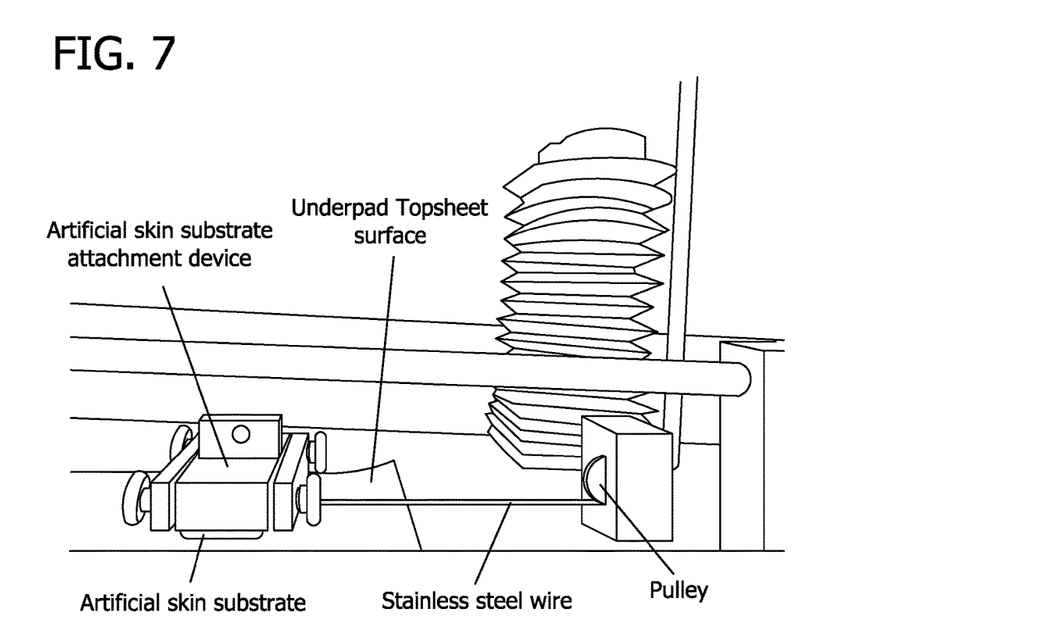
FIG. 7 is an illustration of a portion of the friction measurement apparatus.
Figure 8:
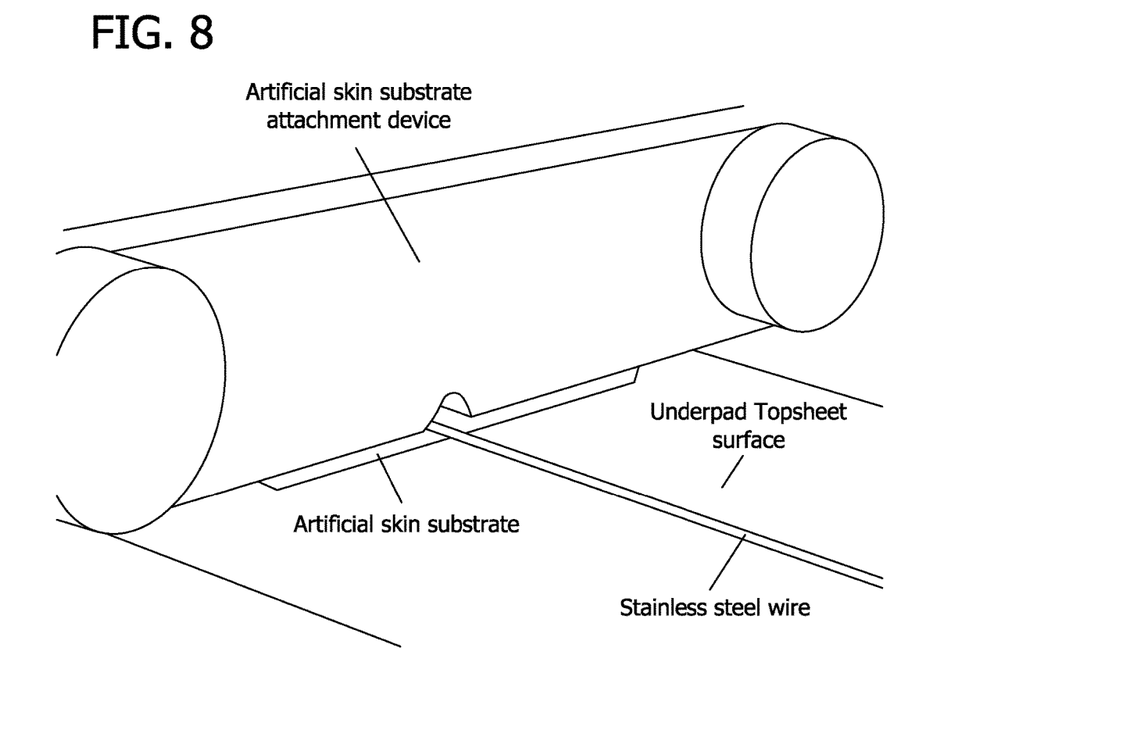
FIG. 8 is an illustration of an underpad in the friction measurement apparatus with the artificial skin attachment device.

A weight was placed on the attachment device to provide an effective load of about 1 psi between the artificial skin and the top sheet of the underpad specimen. To perform each test run, the substrate attachment device was pulled through the steel wire which was routed through a pulley as shown in FIGS. 7 and 8. Static and dynamic friction coefficients were determined using Exponent Stable Micro Systems software for each test run, which were all performed at a temperature of about 70° F. (about 21° C.) and about 50% relative humidity.

Table 1 lists the measured static and kinetic friction coefficients results for several runs for the example underpad (P3036C-Bico+MVP).

The static coefficient of friction of the exemplary underpad was measured to be in a range of from 0.73 to 0.992 and the measured kinetic coefficient of friction was in a range of from 0.558 to 0.859, respectively. Further, the measured average static coefficient of friction and the measured average kinetic coefficient of friction were 0.85 and 0.69, respectively. Thus, this exemplary underpad had an average static coefficient of friction of at least about 0.8 and an average kinetic coefficient of friction of less than about 0.7.

TABLE 1

P3036C - Bico + MVP

| Test Number | Static Friction | Kinetic Friction | Test Number | Static Friction | Kinetic Friction |
|---|---|---|---|---|---|
| 120520121 | 0.757 | 0.624 | 1205201224 | 0.906 | 0.756 |
| 120520122 | 0.730 | 0.577 | 1205201225 | 0.807 | 0.633 |
| 120520124 | 0.749 | 0.569 | 1205201227 | 0.820 | 0.639 |
| 120520125 | 0.837 | 0.668 | 1205201228 | 0.888 | 0.742 |
| 120520126 | 0.765 | 0.597 | 1205201234 | 0.891 | 0.720 |
| 120520128 | 0.815 | 0.623 | 1205201235 | 0.803 | 0.634 |
| 120520129 | 0.844 | 0.683 | 1205201236 | 0.945 | 0.827 |
| 1205201210 | 0.857 | 0.685 | 1205201237 | 0.766 | 0.622 |
| 1205201211 | 0.860 | 0.671 | 1205201239 | 0.948 | 0.778 |
| 1205201212 | 0.871 | 0.694 | 1205201240 | 0.945 | 0.842 |
| 1205201213 | 0.863 | 0.688 | 1205201241 | 0.758 | 0.608 |
| 1205201217 | 0.735 | 0.558 | 1205201242 | 0.803 | 0.638 |
| 1205201218 | 0.885 | 0.742 | 1205201243 | 0.992 | 0.859 |
| 1205201221 | 0.843 | 0.682 | 1205201244 | 0.977 | 0.831 |
| 1205201223 | 0.874 | 0.687 | 1205201245 | 0.962 | 0.811 |
| Average | | | | 0.85 | 0.69 |
| Standard Deviation | | | | 0.075 | 0.085 |

Under substantially the same conditions, comparative test were performed on commercially available underpad products. Tables 2 and 3 list the measured static and kinetic friction coefficients results for several runs for underpad products, ULTRASORB™ and XXL, respectively, each available from Medline Industries, Inc., Mundelein, Ill.

In contrast to the exemplary underpad, the measured average static coefficient of friction of the commercially available ULTRASORB underpad product was 0.9 and the measured average static coefficient of friction was about 0.77. The measured average static coefficient of friction of the commercially available XXL underpad product was about 0.82 and the measured average static coefficient of friction was about 0.78.

TABLE 2

ULTRASORB

| Test Number | Static Friction | Kinetic Friction | Test Number | Static Friction | Kinetic Friction |
|---|---|---|---|---|---|
| 1 | 0.928 | 0.789 | 6 | 0.876 | 0.725 |
| 2 | 0.917 | 0.725 | 7 | 0.936 | 0.855 |
| 3 | 0.870 | 0.664 | 8 | 0.897 | 0.797 |
| 4 | 0.930 | 0.809 | 9 | 0.862 | 0.783 |

TABLE 2-continued

ULTRASORB

| Test Number | Static Friction | Kinetic Friction | Test Number | Static Friction | Kinetic Friction |
|---|---|---|---|---|---|
| 5 | 0.881 | 0.756 | | | |
| Average | | | | 0.900 | 0.767 |
| Standard Deviation | | | | 0.029 | 0.056 |

TABLE 3

XXL

| Test Number | Static Friction | Kinetic Friction | Test Number | Static Friction | Kinetic Friction |
|---|---|---|---|---|---|
| 120520121 | 0.873 | 0.791 | 1205201229 | 0.865 | 0.82 |
| 120520122 | 0.87 | 0.784 | 1205201230 | 0.669 | 0.648 |
| 120520125 | 0.858 | 0.75 | 1205201232 | 0.895 | 0.861 |
| 120520129 | 0.848 | 0.752 | 1205201233 | 0.722 | 0.688 |
| 1205201212 | 0.836 | 0.757 | 1205201234 | 0.865 | 0.832 |
| 1205201213 | 0.818 | 0.728 | 1205201235 | 0.853 | 0.833 |
| 1205201214 | 0.844 | 0.798 | 1205201236 | 0.748 | 0.716 |
| 1205201215 | 0.84 | 0.836 | 1205201237 | 0.874 | 0.841 |
| 1205201218 | 0.874 | 0.811 | 1205201239 | 0.653 | 0.646 |
| 1205201219 | 0.868 | 0.839 | 1205201241 | 0.852 | 0.852 |
| 1205201220 | 0.865 | 0.863 | 1205201242 | 0.651 | 0.649 |
| 1205201221 | 0.804 | 0.732 | 1205201243 | 0.788 | 0.785 |
| 1205201222 | 0.875 | 0.846 | 1205201244 | 0.862 | 0.841 |
| 1205201223 | 0.873 | 0.847 | 1205201245 | 0.857 | 0.831 |
| 1205201224 | 0.718 | 0.691 | 1205201246 | 0.778 | 0.778 |
| 1205201225 | 0.864 | 0.826 | 1205201247 | 0.865 | 0.864 |
| 1205201226 | 0.703 | 0.702 | 1205201248 | 0.803 | 0.802 |
| 1205201227 | 0.654 | 0.648 | 1205201250 | 0.862 | 0.85 |
| 1205201228 | 0.852 | 0.834 | | | |
| Average | | | | 0.816 | 0.783 |
| Standard Deviation | | | | 0.073 | 0.069 |

While the above description contains many specifics, these specifics should not be construed as limitations on the scope of the present disclosure, but merely as exemplifications of embodiments thereof. It is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Those skilled in the art will envision many other possible variations that are within the scope and spirit of the present disclosure.

What is claimed is:

1. An absorbent article comprising:
   a fluid pervious top sheet having bicomponent fibers, the top sheet comprising the top most layer of the absorbent article such that the bicomponent fibers are positioned to engage a wearer's skin when the absorbent article is worn, the top sheet having an average static coefficient of friction greater than or equal to about 0.8 and an average kinetic coefficient of friction less than or equal to about 0.7, the average static coefficient of friction and the average dynamic coefficient of friction being defined by the frictional engagement between the bicomponent fibers and the wearer's skin when the absorbent article is applied to the wearer's skin;
   a fluid impervious back sheet; and
   an absorbent core positioned between the top sheet and the back sheet.

2. The absorbent article of claim 1, wherein the absorbent core comprises at least one superabsorbent section comprising superabsorbent polymer particles.

3. The absorbent article of claim 2, wherein the at least one superabsorbent section comprises a first superabsorbent section and a second superabsorbent section, wherein the first superabsorbent section defines a first zone comprising a first amount of superabsorbent polymer particles and the second superabsorbent section defines a second zone comprising a second amount of superabsorbent polymer particles, the first amount of superabsorbent polymer particles being greater than the second amount of superabsorbent polymer particles.

4. The absorbent article of claim 3, wherein the first zone comprises greater than or equal to about 70 wt % of superabsorbent polymer particles and less than or equal to about 30 wt % fluff pulp.

5. The absorbent article of claim 1, wherein the absorbent core comprises a matrix of fluff pulp.

6. The absorbent article of claim 1, wherein the top sheet consists essentially of bicomponent fibers having about a polyethylene sheath around a polypropylene core.

7. The absorbent article of claim 1, wherein the top sheet has an outer layer of spun bond bicomponent fibers, a second layer of melt blown bicomponent fibers, and a third layer of spun bond bicomponent fibers.

8. The absorbent article of claim 1, wherein the average static coefficient of friction of the top sheet is in a range of from about 0.8 to 1.

9. The absorbent article claim 8, wherein the average kinetic coefficient of friction of the top sheet is in a range of from about 0.5 to 0.7.

10. A method of fabricating an absorbent article, comprising:
providing a fluid pervious top sheet having bicomponent fibers in an amount sufficient to provide the top sheet with an average static coefficient of friction greater than or equal to about 0.8 and an average dynamic coefficient of friction less than or equal to about 0.7, the top sheet comprising the top most layer of the absorbent article such that the bicomponent fibers are positioned to engage a wearer's skin when the absorbent article is worn, the average static coefficient of friction and the average dynamic coefficient of friction being defined by the frictional engagement between the bicomponent fibers and the wearer's skin when the absorbent article is applied to the wearer's skin;
providing a fluid impervious back sheet; and
positioning an absorbent core between the top sheet and the back sheet.

11. The method of claim 10, wherein providing the top sheet comprises providing a first layer of spun bond bicomponent fibers, providing a second layer of melt blown bicomponent fibers, and providing a third layer of spun bond bicomponent fibers.

12. The method of claim 11, wherein providing the first layer comprises selecting the amount of the bicomponent fibers sufficient to achieve an average static coefficient of friction in a range of from about 0.8 to 1 and an average kinetic coefficient of friction in a range of from about 0.5 to 0.7.

13. The method of claim 10, wherein providing the top sheet comprises providing a first layer of spun bond bicomponent fibers, providing a second layer of spun bond bicomponent fibers, and providing a third layer of spun bond bicomponent fibers, wherein the average static coefficient of friction of the first layer is in a range of from about 0.8 to 1 and the average kinetic coefficient of friction of the first layer is in a range of from about 0.5 to 0.7.

14. The method of claim 10, wherein the top sheet consists essentially of bicomponent fibers.

15. The article of claim 1, wherein the top sheet is in contact with the absorbent core.

16. The article of claim 1, wherein the top sheet extends beyond an edge of the absorbent core.

17. The article of claim 1, wherein the absorbent core is surrounded by peripheral regions of the top sheet and the back sheet.

18. The absorbent article of claim 2, further comprising a second superabsorbent section comprising superabsorbent polymer particles, wherein the first superabsorbent section is spaced from the second superabsorbent section defining a channel extending longitudinally along the absorbent article.

19. The absorbent article of claim 1 wherein the bicomponent fibers include a constituent component having a crystallization temperature selected to provide the average static coefficient of friction and the average dynamic coefficient of friction.

* * * * *